United States Patent [19]

Kim

[11] Patent Number: 5,583,053
[45] Date of Patent: Dec. 10, 1996

[54] MACROPHAGE CELL LINE FOR USE IN THE DETECTION OF ANTINUCLEAR ANTIBODIES

[76] Inventor: Think Y. Kim, 1207, 7-tong Hanyang Apt., Jayang-dong, Seongdong-ku, Seoul 133-190(KR), Rep. of Korea

[21] Appl. No.: 196,220

[22] PCT Filed: Jul. 21, 1993

[86] PCT No.: PCT/KR93/00061

§ 371 Date: Mar. 17, 1994

§ 102(e) Date: Mar. 17, 1994

[87] PCT Pub. No.: WO94/02594

PCT Pub. Date: Feb. 3, 1994

[30] Foreign Application Priority Data

Jul. 21, 1992 [KR] Rep. of Korea ................. 1992-12927
Jul. 21, 1992 [KR] Rep. of Korea ................. 1992-12928

[51] Int. Cl.$^6$ ................................................. G01N 33/564
[52] U.S. Cl. ........................ 436/508; 422/57; 435/7.24; 435/240.2; 435/970
[58] Field of Search ................................ 435/7.2, 7.21, 435/7.24, 960, 40.51, 29, 6, 240.21, 240.2, 240.25, 970; 436/508, 509, 519, 506; 422/50

[56] References Cited

U.S. PATENT DOCUMENTS 4,487,830 12/1984 Coates et al. ............................... 435/7

FOREIGN PATENT DOCUMENTS 0205387 12/1986 European Pat. Off. .
1520646 8/1978 Germany .
91/12316 8/1991 WIPO .

OTHER PUBLICATIONS

Sundstrom, C. and K. Nilsson. "Establishment and characterization of a human histiocytic lymphoma cell line (U-937)." *International Journal of Cancer*, vol. 17 (1976), pp. 565–577.

Wing, E. J. and J. S. Remington. "Delayed hypersensitivity and macrophage functions." in: Basic and Clinical Immunology, 3rd edition, (Lange Medical Publications, 1980), p. 134.

*Primary Examiner*—James C. Housel
*Assistant Examiner*—Prasad Murthy
*Attorney, Agent, or Firm*—Foley & Lardner

[57] ABSTRACT

The macrophage cell line, IT-1 (KCCM-10038) was derived from normal human bone marrow. IT-1 cells are characterized by excellent adherence onto glass slides used in immunofluorescence assays, and the cells provide a positive result in the antinuclear antibody (ANA) test. Moreover, ANA tests performed with IT-1 cells were found to be more reliable and more easily interpreted than ANA tests performed with the customary HEp-2 cell line. Accordingly, IT-1 cells are particularly suitable for the diagnosis of autoimmune disease using the ANA test.

8 Claims, 1 Drawing Sheet

MACROPHAGE CELL LINE FOR USE IN THE DETECTION OF ANTINUCLEAR ANTIBODIES

FIELD OF THE INVENTION

This invention, related to the macrophage cell line, IT-1, is a method for detecting an antinuclear antibody (abbreviated as ANA, hereinafter) by employing the said macrophage cell line and a slide preparation.

BACKGROUND OF THE INVENTION

The ANA test for detecting the presence of an autoantibody in the serum or any other body fluid is applied to autoimmune diseases such as systemic lupus erythematosus (hereinafter, abbreviated as SLE), Sjoegren's syndrome, systemic sclerosis, mixed connective tissue disease, rheumatoid arthritis, juvenile chronic polyarthritis and other autoimmune diseases.

When a patient is initially thought to have a systemic rheumatic disease by the ANA test, the precise disease is diagnosed through a definite antibody identifying test against antigens such as DNA, histone, extractable nuclear antigens (ENA) such as Sm (Smith), nRNP (nuclear ribonucleoprotein), SS-A (Sjoegren's syndrome antigen A), SS-B, Scl-70, Jo-1, rRNP, etc.

The characteristics and titer of the antibody were standardized by using the standard serum developed from AF-CDC (Arthritis Foundation-Centers for Disease Control) in 1982 (Arthritis Rheum. 25, 1003, 1982) and concurrently, in an examination utilizing an immunofluorescence assay. The inconsistency or qualitical differences between the fluorescent microscopes employed, the concentration of FITC (fluorescein isothiocyanate) conjugated antisera and fluorescent label/protein (f/p) ratio were improved by employing an optical slide with graded degrees of fluorescence (Am. J. Clin. Path., 82, 57, 1984).

The most important factor in FANA (fluorescent antinuclear antibody), a test which is essential to the diagnosis of an autoimmune disease, is the selection of a substrate. In earlier ANA tests, cryostat tissue sections of organs such as the livers or kidneys of experimental animals had been used as the substrate. Recently, cultured human cells have mainly been used. An example of cultured human cells is the HEp-2 cell (ATCC CCL-23). By employing said cultured human cells, the species-genus specificity or the organ specificity could be overcome.

Since cultured human cells generally possess a larger nucleus and contain higher contents and a greater variety of specific nuclear antigens in comparison with the cryostat tissue section, an interpretation of the fluorescent pattern is easier and the possibility of false-negative results can be significantly decreased.

When the cell lines mentioned above were cultured on a slide, mitotic cells could be observed, and using these mitotic cells, it became possible to detect the anti-centromere antibody, anti-PCNA (proliferating cell nuclear antigen), an antibody which is found only in proliferating cells, etc. and to interpret the indistinguishable fluorescent patterns more precisely and objectively.

Although the HEp-2 cell was derived from a human, it is a tumor cell isolated from the laryngeal carcinoma, and when the cell was cultured on a slide without any pretreatment, its glass adherence did not reach a satisfactory level. Moreover, another defect was that ANA is not detected in some patients, which is termed "ANA negative lupus".

To improve the defects mentioned above, the inventor tried to develop a new substrate, and as a result, discovered that the macrophage cell line (IT-1, KCCM-10038) derived from normal bone marrow does not have the above defects and can be employed as a useful substrate for the ANA test.

The theoretical background for research of macrophage as the substrate for the ANA test is as follows:

First, since the macrophage serves as an antigen presenting cell in an immune response, it is highly presumable for the cell to contain autoimmune antigens evenly and abundantly for the purpose of distinguishing self from nonself;

Second, since the glass adherence of the macrophage is excellent, the preparation of a slide for substrate is easy and economical; and Third, since the IT-1 cell is one of nontumor origin, the possibility of false-negative results in the ANA test can be lowered.

It has been a common opinion that the normal human macrophage can not establish a cell line by culture. However, as described in the examples hereunder, the inventor has succeeded in the establishment of the macrophage cell line, thereby completing the present invention.

SUMMARY OF THE INVENTION

It is therefore, an object of this invention to provide a macrophage cell line which can be utilized as a substrate in the ANA test.

Another object is to provide a method for detecting an antinuclear antibody by employing said macrophage cell lines.

It is yet another object of this invention to provide a slide for the ANA test, on which said macrophage cell lines are immobilized.

The goals and advantages of this invention will become apparent as the detailed descriptions follow.

DETAILED DESCRIPTION OF THE INVENTION

The macrophage employed in the establishment of the cell line of this invention was isolated by aspiration of normal human bone marrow (or any other organs) under aseptic conditions.

The macrophage cell line was established by continuously culturing the isolated macrophage in RPMI-1640 medium supplemented with 5–20% fetal calf serum. It was also possible to culture the macrophage in Ham's F12K medium or in Dulbecco's Modified Eagle's medium. Moreover, when about 0.1 ml of macrophage was inoculated in to the RPMI-1640 medium with a concentration of $1\times10^5$ cells/ml which was supplemented with 10% fetal calf serum and in the absence of other additives such as vitamins, etc., cells were observed to proliferate densely showing excellent proliferation in only a few days.

The cell line established in the manner mentioned above was designated as "IT-1".

In general, macrophage cell lines can be attached onto a glass slide for the ANA test. For example, a cultured IT-1 cell suspension was diluted with a RPMI-1640 medium with fetal calf serum added and inoculated onto a slide and after 18 to 30 hours in an incubator (30°–42° C.), the cell line was fixed, using an organic polar solvent such as methanol, ethanol, acetone, etc.

The preparation of a slide for the ANA test by employing the macrophage cell line IT-1 offers many advantages such as the decrease of an inferior product, saving of the cell line inoculated as well as the culture medium and culture time due to the excellent glass adherent properties of the IT-1.

ANA testing employing the IT-1 can be carried out as follows. The IT-1 was contacted with the test serum or any other body fluid such as the cerebrospinal fluid, pleural fluid, joint fluid, etc. and reacted with FITC-labeled rabbit antibody against human gammaglobulin. Afterwards, the fluorescent pattern was observed under a fluorescent microscope.

The characteristics of IT-1 provided by this invention are described as follows;
1. morphology IT-1 mainly shows the form of epithelioid cells and occasionally, macrophage-like and multinucleated giant cell forms can also be observed.
2. size IT-1 is 1.5 times larger than the HEp-2 cell.
3. cytochemistry (Color Atlas of Clinical Hematology 50, Igaku-Shoin, 1986)

α-naphthyl acetate esterase; strong positive
Periodic Acid-Schiff; positive
Naphthol ASD chloroacetate esterase; negative
Peroxidase; negative
Sudan black B; negative
4. lysosomal activity When staining with Acridine orange, large numbers of orange-red lysosome granules were observed in the circumferential part of the nucleus (Atlas of Blood Cells 195, Lea & Febiger, 1988).
5. Fc receptor and phagocytosis When culturing with latex particles coated with immunoglobulin G (IgG) (Behringwerke AG, Germany), large numbers of latex particles were seen to adhere to the external membrane of the IT-1 cell and phagocytosis was also observed.

Along with the characteristics mentioned above, the IT-1 is also proved to be a macrophage based on Zena Werb's classification (Basic & Clinical Immunology, 98, Appleton & Lange, 1987).

Furthermore, when 1000 Units/ml of τ-interferon (LBD-001, Lucky Corporation, Korea) was added, the proliferation of IT-1 was discontinued and the expression of HLA-DR was increased: 5 µl of Anti-HLA-DR-FITC (Beckton-Dickinson Immunocytometry Systems, U.S.A.) was diluted with RPMI medium to 1:10; 50 µl of IT-1 cell ($1\times10^6$) suspension was then added; the reaction mixture was reacted for 30 minutes in an ice-water bath, washed with PBS (Phosphate Buffered Saline) and observed under a fluorescent microscope.

By all the descriptions mentioned above, it is clearly verified that the IT-1 is a responsive macrophage.

Figure 1:
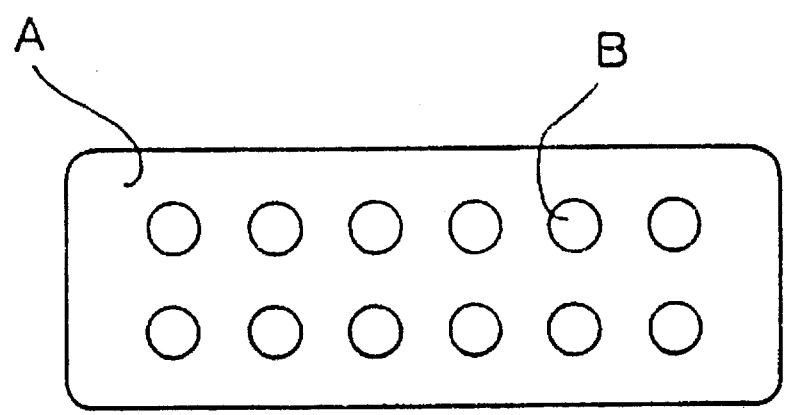
FIG. 1 shows an IF slide provided by the invention in its actual size. In this Figure, A represents glass and B (depicted in small circles), the macrophage cell line immobilized on the slide.

The examples which follow serve to illustrate the invention in greater detail, without limiting the latter.

EXAMPLE 1

Isolation of the Macrophage and Establishment of the Cell Line

Bone marrow cell fluid was taken by aspiration from normal bone marrow, poured into a centrifuging tube and subjected to centrifugation for 30 minutes at 20° C., 400 g to obtain mononuclear cells. Into a 75 ml culture flask containing 15 ml of RPMI-1640 (Gibco Laboratories, U.S.A.) supplemented with 10% fetal calf serum, the mononuclear cells obtained above were inoculated, cultured in a incubator (37° C.) controlled with 5% carbon dioxide for 3 days, and then washed with the culture medium to remove non-adhered cells such as lymphocytes. Cells adhered to the culture flask were proliferated continuously with RPMI-1640 supplemented with 20% fetal calf serum and at the end of 7 days, treated with trypsin. The culturing and proliferating process as described above was repeated in two culture flasks for the trypsin-treated cells, and at the end of 5 days, a second trypsin treatment was carried out. Then, the second trypsin-treated cells were allotted to 4 culture flasks and subjected to the culturing process. The culture medium was changed for a new one every 3 days, and at the end of 28 days, a culture medium in which the concentration of fetal calf serum supplemented was decreased to 10% was employed. The macrophage cell line IT-1 was established in this manner.

The macrophage cell line IT-1 was deposited with the Korean Federation of Culture Collection of Microorganisms (KFCC) on Jul. 15, 1992 (receipt number: KFCC-10772). The relevant deposit was converted to a Budapest Treaty deposit on Jul. 14, 1993 and designated as receipt number "KCCM-10038" in the permanent culture collection of the Korean Culture Center of Microorganisms (KCCM), Department of Food Engineering, College of Engineering, Yonsei University, Sodaemun-gu, Seoul 120-749, Korea.

EXAMPLE 2

Preparation of the Slide

The IT-1 cell suspension cultured as in example 1 was diluted with the RPMI-1640 medium supplemented with 10% fetal calf serum to a concentration of $2\times10^4$ cell/ml and 30 µl of the cell suspension was inoculated into each well of the multiwelled slide for the immunofluorescent procedure (abbreviated as IF slide, hereinafter) after the slide was sterilized. The cell suspension was cultured in an incubator (37° C.) controlled with 5% carbon dioxide for a period of 24 hours. Then, the culture fluid was removed from each well of the slide, washed with PBS and immersed in 95% methanol for 10 minutes to fix the cells. The slide prepared in this manner can be stored for about 1 year at 4° C.

COMPARATIVE EXAMPLE

Preparation of a Slide by Employing HEp-2 Cell

As the comparative example, a method for preparing a slide by culturing the HEp-2 cell line is described hereunder because the commercially available slides for ANA testing employ the said HEp-2 cell.

HEp-2 cells were diluted with the RPMI-1640 medium supplemented with 10% fetal calf serum to a concentration of $1\times10^5$ cell/ml and 30 µl of the cell suspension was inoculated onto several IF slides. When the cells were precipitated and adhered, 120 µl of the medium was additionally allotted to each well to cover the surface of the slide with the medium. The cells were then cultured in a incubator (37° C.) controlled with 5% carbon dioxide for 48 hours. The culture medium was removed from the slide, washed with PBS and immersed in 95% methanol for 10 minutes to fix the cells.

EXAMPLE 3

ANA Test Employing the Cell Line

AF-CDC standard serum #1, #2, #3 and #6 were diluted twofold to give serum solutions a ratio ranging from 1:20 to 1:1280. Thirty microliters of each solution was layered over the IT-1 and HEp-2 slides and let to react at room temperature under high humidity conditions for 30 minutes. The reacted slides were placed into a Coplin jar containing PBS, agitated at 200 rpm on the oscillating shaker, washed and then dried. Thirty microliters of FITC-labeled rabbit antibody against human gammaglobulin (diluted to 1:40) was applied on each slide and let to react at room temperature under high humidity conditions for 30 minutes. Then, each slide was washed with PBS for 10 minutes, counter-stained with 0.2% Evans' blue solution (stored with a preservative at 4° C.) and washed again with PBS. The remaining PBS was removed by filter paper and the fluorescent pattern was observed by using a glycerol-PBS solution at 400 times magnification under a fluorescent microscope.

The fluorescent pattern for the standard serum #1 showed that all the resting cells and the mitotic cells were stained over the entire nucleus or around the nucleus only. The fluorescent pattern for the standard serums #2 and #3 showed a speckled type, that is, partially non-stained sections were present. The fluorescent pattern for the standard serum #6 showed a nucleolar pattern. The above results for the standard serums #2, #3 and #6 were observed in resting cells only. These results correspond to the fluorescent pattern proposed by AF-CDC.

In addition, the intensity of fluorescence was graded and the titer depending on dilution ratio was estimated. The results are listed in Table 1.

| Grade | Intensity of fluorescence |
| --- | --- |
| 4+ | intense |
| 3+ | sufficient |
| 2+ | distinguishable |
| 1+ | barely distinguishable |

As shown in Table 1, in cases employing HEp-2 cells, the standard serums #1, #2 and #6 showed sufficient fluorescence at the dilution ratio of 1:320 and the standard serum #3 also showed sufficient fluorescence at the dilution ratio of 1:640. In cases employing IT-1 cells, the same pattern as in cases of HEp-2 cells was observed. AF-CDC recommended that the dilution ratio of the serum should be in the range of 1:160 to 1:640 for the standard serums #1 and #3 and in the range of 1:80 to 1:320 for the standard serums #2 and #6. Both the HEp-2 cell and the IT-1 cell were included within the AF-CDC recommended extent.

TABLE 1

Comparison of titers for AF-CDC standard serums

| dilution ratio | standard serum #1 | | standard serum #2 | | standard serum #3 | | standard serum #6 | |
| --- | --- | --- | --- | --- | --- | --- | --- | --- |
|  | HEp-2 | IT-1 | HEp-2 | IT-1 | HEp-2 | IT-1 | HEp-2 | IT-1 |
| 1:20 | 4+ | 4+ | 4+ | 4+ | 4+ | 4+ | 4+ | 4+ |
| 1:40 | 4+ | 4+ | 4+ | 4+ | 4+ | 4+ | 4+ | 4+ |
| 1:80 | 4+ | 4+ | 4+ | 4+ | 4+ | 4+ | 4+ | 4+ |
| 1:160 | 4+ | 4+ | 4+ | 4+ | 4+ | 4+ | 3+ | 4+ |
| 1:320 | 3+ | 3+ | 3+ | 3+ | 4+ | 3+ | 3+ | 3+ |
| 1:640 | 1+ | 2+ | 1+ | 2+ | 3+ | 3+ | 2+ | 2+ |
| 1:1280 | — | 1+ | 1+ | — | 2+ | 1+ | 1+ | 1+ |

Other standard serums (AF-CDC standard serums #4, #5, #7, #8 and #9) were additionally applied onto the IT-1 slide and the fluorescent pattern that appeared with each serum was observed in the same manner as described above. In this test, AF-CDC #4 and #5 showed a speckled type up to the dilution ratio of 1:1280; #7 also showed a speckled type up to the dilution ratio of 1:320; #8 showed a discrete speckled type and a positive response to mitotic cells was also observed; and #9 showed a speckled type up to the dilution ratio of 1:640.

In addition, the standard serums supplied by Immunovision, Inc. U.S.A., were also subjected to the ANA test, and as the result, both anti-Jo-1 and anti-rRNP showed the fluorescent pattern of a cytoplasmic type up to the dilution ratio of 1:320 (anti-Jo-1) and 1:640, (anti-rRNP) respectively.

On microscopic observation, if the cells were adhered to all of the 12 wells, the interpretation of the fluorescent pattern would be easy. However, cells are occasionally peeled from the well and this inferior ratio was measured to be 9/600 for IT-1 and 95/600 for HEp-2. From the result above, it can easily be presumed that IT-1 shows excellent adherence. There were, other advantages such as the number of cells inoculated onto a slide and the contents of the culture medium could be decreased to one-fifth and the culture time could be reduced by half.

EXAMPLE 4

Application to Clinical Experiments

A clinical experiment was made with the sera taken from 67 patients carrying an anti-SS-A/Ro antibody only, which is liable to show a false-negative result on the ANA test (confirmed by double immunodiffusion assay). The result showed a positive reaction in the proportion of 100% for the ANA test employing the IT-1 and 88% for that of HEp-2.

In another experiment with three groups of patients (the number of patients with SLE, 61 (group A); systemic sclerosis, 20 (Group B); and mixed connective tissue disease, 18 (group C)), the ANA test employing HEp-2 induced a positive response in the proportion of 95% (A), 85% (B) and 100% (C) and that employing IT-1 induced a positive response in the proportion of 100% (A), 95% (B) and 100% (C). The results above prove that the ANA test could be accomplished more precisely by employing the macrophage cell line IT-1 according to this invention.

It should be understood that the examples and embodiments described herein are for illustrative purposes only and that various modifications or changes in light thereof will be suggested to persons skilled in the art and are to be included within the spirit and purview of this invention and the scope of the appended claims.

What is claimed is:

1. A macrophage cell line, wherein said cell line has at least one antigenic epitope that specifically binds a human antinuclear antibody, and wherein said macrophage cell line is IT-1 (KCCM-10038).

2. A microwell slide for detecting antinuclear antibodies, wherein said slide contains macrophage cells immobilized to the microwells, and wherein said macrophage cells are either the cell line IT-1 (KCCM-10038) or progeny thereof.

3. A method for detecting antinuclear antibodies in a human body fluid sample, comprising the steps of:

(A) contacting a human body fluid sample with macrophage cells from the macrophage cell line IT-1 (KCCM-10038) derived from normal human bone marrow, wherein said cells have antigenic epitopes that specifically bind human antinuclear antibodies; and (B) detecting antibody binding to said macrophage cells.

4. A method according to claim 3, wherein said sample is taken from a patient having an autoimmune disease.

5. A method according to claim 3, wherein said detecting step, B, is effected by contacting said macrophage cells with anti-human immunoglobulin that comprises a label, and detecting said label bound to said macrophage cells.

6. A method according to claim 3, wherein said macrophage cells are immobilized into slide wells.

7. A method according to claim 3, wherein said antigenic epitopes are selected from the group consisting of deoxyribonucleic acid epitope, histone epitope and nuclear antigen epitope.

8. A method according to claim 7, wherein said nuclear antigen epitope is part of a protein selected from the group consisting of Smith, nuclear ribonucleoprotein, Sjoegren's syndrome antigen A, SS-B, Scl-70, Jo-1, rRNP and proliferating cell nuclear antigen.

* * * * *